United States Patent
Sherwood et al.

(10) Patent No.: US 11,191,457 B2
(45) Date of Patent: Dec. 7, 2021

(54) GAS SAMPLING CATHETERS, SYSTEMS AND METHODS

(71) Applicant: Boston Scientific Scimed, Inc., Maple Grove, MN (US)

(72) Inventors: Gregory J. Sherwood, North Oaks, MN (US); Justin Theodore Nelson, St. Louis Park, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 629 days.

(21) Appl. No.: 15/621,103

(22) Filed: Jun. 13, 2017

(65) Prior Publication Data

US 2017/0360337 A1 Dec. 21, 2017

Related U.S. Application Data

(60) Provisional application No. 62/350,345, filed on Jun. 15, 2016.

(51) Int. Cl.
*A61B 5/145* (2006.01)
*A61M 25/00* (2006.01)
(Continued)

(52) U.S. Cl.
CPC ........ *A61B 5/14503* (2013.01); *A61B 5/0538* (2013.01); *A61B 5/065* (2013.01);
(Continued)

(58) Field of Classification Search
None
See application file for complete search history.

(56) References Cited

U.S. PATENT DOCUMENTS

| 3,661,528 A | 5/1972 | Falk |
| 3,952,730 A * | 4/1976 | Key ............ A61B 5/145 600/364 |

(Continued)

FOREIGN PATENT DOCUMENTS

| CN | 102941042 | 2/2013 |
| CN | 103332678 | 10/2013 |

(Continued)

OTHER PUBLICATIONS

Communication Pursuant to Article 94(3) EPC for European Patent Application No. 18180455.0 dated Jul. 15, 2019 (5 pages).

(Continued)

*Primary Examiner* — Sean P Dougherty
*Assistant Examiner* — Benjamin S Melhus
(74) *Attorney, Agent, or Firm* — Pauly, DeVries Smith & Deffner LLC

(57) ABSTRACT

Embodiments herein include gas sampling catheters, systems and related methods. In an embodiment, a gas sampling catheter is included. The catheter can include a catheter shaft having a proximal end and a distal end, the catheter shaft defining a lumen therein. The catheter can include a gas sampling port providing fluid communication between the exterior of the catheter shaft adjacent the distal end of the lumen of the catheter shaft. The catheter can further include a sensor element disposed in fluid communication with the lumen, the sensor element configured to detect a component of a gaseous sample. The sensor element can include a first measurement zone comprising a plurality of discrete binding detectors. Other embodiments are also included herein.

19 Claims, 9 Drawing Sheets

(51) Int. Cl.
*A61B 5/03* (2006.01)
*G01N 33/483* (2006.01)
*A61B 5/0538* (2021.01)
*A61B 5/00* (2006.01)
*A61B 5/06* (2006.01)
*A61B 10/00* (2006.01)
*A61B 10/04* (2006.01)

(52) U.S. Cl.
CPC ......... *A61B 5/6852* (2013.01); *A61M 25/003* (2013.01); *A61M 25/0067* (2013.01); *A61B 5/03* (2013.01); *A61B 10/04* (2013.01); *A61B 2010/0083* (2013.01); *A61M 25/0071* (2013.01); *A61M 2025/0002* (2013.01); *A61M 2025/0031* (2013.01); *G01N 33/483* (2013.01)

(56) References Cited

U.S. PATENT DOCUMENTS

| | | | |
|---|---|---|---|
| 3,981,297 A * | 9/1976 | Dunn | A61B 5/145 600/364 |
| 4,901,727 A * | 2/1990 | Goodwin | A61B 5/145 600/364 |
| 5,174,290 A * | 12/1992 | Fiddian-Green | A61B 5/145 600/364 |
| 5,186,172 A * | 2/1993 | Fiddian-Green | A61B 5/145 600/353 |
| 5,357,971 A | 10/1994 | Sheehan et al. | |
| 5,423,320 A * | 6/1995 | Salzman | A61B 5/1459 600/473 |
| 5,704,368 A | 1/1998 | Asano et al. | |
| 5,834,626 A | 11/1998 | De Castro et al. | |
| 5,928,155 A * | 7/1999 | Eggers | A61B 5/0215 600/526 |
| 6,006,121 A * | 12/1999 | Vantrappen | A61B 5/14542 600/343 |
| 6,029,076 A * | 2/2000 | Fiddian-Greene | A61B 5/036 600/353 |
| 6,085,576 A | 7/2000 | Sunshine et al. | |
| 6,149,624 A | 11/2000 | McShane | |
| 6,192,168 B1 | 2/2001 | Feldstein et al. | |
| 6,238,339 B1 * | 5/2001 | Fiddian-Greene | A61B 5/036 600/309 |
| 6,248,078 B1 | 6/2001 | Risby et al. | |
| 6,312,390 B1 | 11/2001 | Phillips et al. | |
| 6,480,734 B1 | 11/2002 | Zhang et al. | |
| 6,599,253 B1 | 7/2003 | Baum et al. | |
| 6,615,066 B2 * | 9/2003 | Huybrechts | A61B 5/14542 600/343 |
| 6,712,770 B2 | 3/2004 | Lin et al. | |
| 6,726,637 B2 | 4/2004 | Phillips et al. | |
| 6,781,690 B2 | 8/2004 | Armstrong et al. | |
| 6,955,652 B1 | 10/2005 | Baum et al. | |
| 6,978,182 B2 | 12/2005 | Mazar et al. | |
| 7,032,431 B2 | 4/2006 | Baum et al. | |
| 7,123,359 B2 | 10/2006 | Armstrong et al. | |
| 7,177,686 B1 | 2/2007 | Turcott et al. | |
| 7,426,848 B1 | 9/2008 | Li et al. | |
| 7,459,312 B2 | 12/2008 | Chen et al. | |
| 7,704,214 B2 | 4/2010 | Meixner et al. | |
| 7,809,441 B2 | 10/2010 | Kane et al. | |
| 7,871,572 B2 | 1/2011 | Yang et al. | |
| 7,972,277 B2 | 7/2011 | Oki et al. | |
| 7,988,917 B2 | 8/2011 | Roesicke et al. | |
| 7,992,422 B2 | 8/2011 | Leddy et al. | |
| 8,043,860 B2 | 10/2011 | Leznoff et al. | |
| 8,052,933 B2 | 11/2011 | Schirmer et al. | |
| 8,080,206 B2 | 12/2011 | Leddy et al. | |
| 8,124,419 B2 | 2/2012 | Grigorian et al. | |
| 8,153,439 B2 | 4/2012 | Zamborini et al. | |
| 8,154,093 B2 | 4/2012 | Passmore et al. | |
| 8,157,730 B2 | 4/2012 | Tucker et al. | |
| 8,222,041 B2 | 7/2012 | Pearton et al. | |
| 8,244,355 B2 | 8/2012 | Bennett et al. | |
| 8,366,630 B2 | 2/2013 | Haick et al. | |
| 8,479,731 B2 | 7/2013 | Heinonen et al. | |
| 8,481,324 B2 | 7/2013 | Nakhoul et al. | |
| 8,494,606 B2 | 7/2013 | Debreczeny et al. | |
| 8,529,459 B2 | 9/2013 | Stahl, Jr. et al. | |
| 8,597,953 B2 | 12/2013 | Haick et al. | |
| 8,747,325 B2 | 6/2014 | Bacal et al. | |
| 8,828,713 B2 | 9/2014 | Ren et al. | |
| 8,835,984 B2 | 9/2014 | Ren et al. | |
| 8,848,189 B2 | 9/2014 | Goldshtein et al. | |
| 8,955,367 B2 | 2/2015 | Gouma et al. | |
| 9,011,779 B1 | 4/2015 | Jensen et al. | |
| 9,029,168 B2 | 5/2015 | Mannoor et al. | |
| 9,103,775 B2 | 8/2015 | Bradley et al. | |
| 9,147,398 B2 | 9/2015 | White et al. | |
| 9,147,851 B1 | 9/2015 | Bartsch et al. | |
| 9,299,238 B1 | 3/2016 | Ahmad et al. | |
| 9,315,848 B2 | 4/2016 | Haick et al. | |
| 9,316,637 B2 | 4/2016 | Ren et al. | |
| 9,324,825 B2 | 4/2016 | Ravesi et al. | |
| 9,366,664 B2 | 6/2016 | Jensen et al. | |
| 9,513,244 B2 | 12/2016 | Koester | |
| 9,528,979 B2 | 12/2016 | Haick et al. | |
| 9,618,476 B2 | 4/2017 | Goldsmith | |
| 9,642,577 B1 | 5/2017 | Li et al. | |
| 9,696,311 B2 | 7/2017 | Haick et al. | |
| 9,763,600 B2 | 9/2017 | Van Kesteren et al. | |
| 9,765,395 B2 | 9/2017 | Goldsmith | |
| 9,936,897 B2 | 4/2018 | Carlson et al. | |
| 9,977,011 B2 | 5/2018 | Beck et al. | |
| 10,034,621 B2 | 7/2018 | Wondka et al. | |
| 10,046,323 B2 | 8/2018 | Bos | |
| 10,307,080 B2 | 6/2019 | Ssenyange et al. | |
| 10,770,182 B2 | 9/2020 | Sherwood et al. | |
| 10,852,264 B2 | 12/2020 | Kelly et al. | |
| 2002/0123749 A1 | 9/2002 | Jain et al. | |
| 2002/0142477 A1 | 10/2002 | Lewis et al. | |
| 2003/0051733 A1 | 3/2003 | Kotmel et al. | |
| 2004/0039295 A1 | 2/2004 | Olbrich et al. | |
| 2006/0130557 A1 | 6/2006 | Leddy et al. | |
| 2006/0263255 A1 | 11/2006 | Han et al. | |
| 2006/0270940 A1 | 11/2006 | Tsukashima et al. | |
| 2007/0048181 A1 | 3/2007 | Chang et al. | |
| 2007/0083094 A1 | 4/2007 | Colburn et al. | |
| 2007/0167853 A1 | 7/2007 | Melker et al. | |
| 2007/0229818 A1 | 10/2007 | Duan et al. | |
| 2007/0265509 A1 | 11/2007 | Burch et al. | |
| 2008/0021339 A1 | 1/2008 | Gabriel et al. | |
| 2008/0038154 A1 | 2/2008 | Longbottom et al. | |
| 2008/0146890 A1 | 6/2008 | Leboeuf et al. | |
| 2008/0161709 A1 | 7/2008 | Bradley | |
| 2008/0183910 A1 | 7/2008 | Natoli et al. | |
| 2008/0228098 A1 | 9/2008 | Popov et al. | |
| 2008/0317636 A1 | 12/2008 | Brahim et al. | |
| 2009/0054799 A1 | 2/2009 | Vrtis et al. | |
| 2009/0112115 A1 | 4/2009 | Huang et al. | |
| 2010/0024533 A1 | 2/2010 | Kimura et al. | |
| 2010/0056892 A1 * | 3/2010 | Ben-Barak | A61B 5/073 600/354 |
| 2010/0085067 A1 | 4/2010 | Gabriel et al. | |
| 2010/0137733 A1 | 6/2010 | Wang et al. | |
| 2010/0147303 A1 | 6/2010 | Jafari et al. | |
| 2010/0188069 A1 | 7/2010 | Ren et al. | |
| 2010/0198521 A1 | 8/2010 | Haick et al. | |
| 2010/0216175 A1 | 8/2010 | Melker et al. | |
| 2010/0273665 A1 | 10/2010 | Haick et al. | |
| 2011/0015872 A1 | 1/2011 | Haick et al. | |
| 2011/0017587 A1 | 1/2011 | Zhamu et al. | |
| 2011/0143962 A1 | 6/2011 | Chaubron et al. | |
| 2011/0201956 A1 * | 8/2011 | Alferness | A61B 1/267 600/532 |
| 2011/0269632 A1 | 11/2011 | Haick et al. | |
| 2011/0283770 A1 | 11/2011 | Hok et al. | |
| 2012/0111093 A1 | 5/2012 | Brahim et al. | |
| 2012/0126111 A1 | 5/2012 | Chaubron et al. | |
| 2012/0156099 A1 | 6/2012 | Zhong et al. | |
| 2012/0166095 A1 | 6/2012 | Potyrailo et al. | |
| 2012/0203081 A1 | 8/2012 | Leboeuf et al. | |
| 2012/0226111 A1 | 9/2012 | Leboeuf et al. | |

(56) References Cited

U.S. PATENT DOCUMENTS

| | | |
|---|---|---|
| 2012/0226112 A1 | 9/2012 | Leboeuf et al. |
| 2012/0245434 A1 | 9/2012 | Haick et al. |
| 2012/0245854 A1 | 9/2012 | Haick et al. |
| 2012/0277794 A1 | 11/2012 | Kountotsis et al. |
| 2012/0306802 A1 | 12/2012 | Mccracken |
| 2012/0326092 A1 | 12/2012 | Haick et al. |
| 2013/0034190 A1 | 2/2013 | Tan et al. |
| 2013/0034910 A1 | 2/2013 | Haick et al. |
| 2013/0059758 A1 | 3/2013 | Haick et al. |
| 2013/0100067 A1 | 4/2013 | Dews |
| 2013/0102018 A1 | 4/2013 | Schentag et al. |
| 2013/0143247 A1 | 6/2013 | Haick et al. |
| 2013/0150261 A1 | 6/2013 | Haick et al. |
| 2013/0165810 A1 | 6/2013 | Saatchi et al. |
| 2013/0171733 A1 | 7/2013 | Haick et al. |
| 2013/0178756 A1 | 7/2013 | Suzuki et al. |
| 2013/0211207 A1 | 8/2013 | Joseph et al. |
| 2013/0211852 A1 | 8/2013 | Roizen et al. |
| 2013/0236981 A1 | 9/2013 | Haick et al. |
| 2013/0253358 A1 | 9/2013 | Phillips et al. |
| 2013/0267862 A1 | 10/2013 | Jaffe et al. |
| 2013/0289368 A1 | 10/2013 | Covington et al. |
| 2013/0331723 A1 | 12/2013 | Hernandez-Silveira et al. |
| 2013/0334579 A1 | 12/2013 | Accardi et al. |
| 2014/0018691 A1 | 1/2014 | Mcneill et al. |
| 2014/0041436 A1 | 2/2014 | Knott et al. |
| 2014/0051956 A1 | 2/2014 | Dalene et al. |
| 2014/0094669 A1 | 4/2014 | Jaffe et al. |
| 2014/0122515 A1 | 5/2014 | Lee et al. |
| 2014/0145735 A1 | 5/2014 | Koester et al. |
| 2014/0171817 A1 | 6/2014 | Blanch et al. |
| 2014/0194703 A1 | 7/2014 | Wondka et al. |
| 2014/0275597 A1 | 9/2014 | Zhang et al. |
| 2014/0275854 A1 | 9/2014 | Venkatraman et al. |
| 2014/0276168 A1 | 9/2014 | Vissapragada Venkata Satya et al. |
| 2014/0294675 A1 | 10/2014 | Melker et al. |
| 2014/0318535 A1 | 10/2014 | Bullock et al. |
| 2014/0378790 A1 | 12/2014 | Cohen |
| 2015/0013429 A1 | 1/2015 | Atkin et al. |
| 2015/0038378 A1 | 2/2015 | Cheng et al. |
| 2015/0044710 A1 | 2/2015 | Dasgupta et al. |
| 2015/0065365 A1 | 3/2015 | Ahmad |
| 2015/0164373 A1* | 6/2015 | Davis ............... A61B 5/082 600/532 |
| 2015/0196251 A1 | 7/2015 | Outwater et al. |
| 2015/0257676 A1 | 9/2015 | Fries |
| 2015/0265184 A1 | 9/2015 | Wondka et al. |
| 2015/0295562 A1 | 10/2015 | Agarwal et al. |
| 2015/0301021 A1 | 10/2015 | Haick et al. |
| 2015/0307936 A1 | 10/2015 | Goldsmith |
| 2015/0309018 A1 | 10/2015 | Goldsmith |
| 2015/0320338 A1 | 11/2015 | Kane et al. |
| 2015/0335266 A1 | 11/2015 | Cormier |
| 2015/0335267 A1 | 11/2015 | Cormier et al. |
| 2015/0338340 A1 | 11/2015 | Jiang et al. |
| 2015/0338390 A1 | 11/2015 | Anglin et al. |
| 2015/0351699 A1 | 12/2015 | Addison et al. |
| 2016/0025675 A1 | 1/2016 | Goldsmith |
| 2016/0054312 A1 | 2/2016 | Goldsmith |
| 2016/0089089 A1 | 3/2016 | Kakkar et al. |
| 2016/0109440 A1 | 4/2016 | Sherwood et al. |
| 2016/0116431 A1 | 4/2016 | Accardi et al. |
| 2016/0150995 A1 | 6/2016 | Ratto et al. |
| 2016/0157752 A1 | 6/2016 | Cho et al. |
| 2016/0192861 A1 | 7/2016 | Gedeon et al. |
| 2016/0231309 A1 | 8/2016 | Ahmad et al. |
| 2016/0334381 A1 | 11/2016 | King-smith et al. |
| 2016/0370337 A1 | 12/2016 | Blackley |
| 2017/0014043 A1 | 1/2017 | Mcdonnell |
| 2017/0042435 A1 | 2/2017 | Vermeulen et al. |
| 2017/0053068 A1 | 2/2017 | Pillai et al. |
| 2017/0227491 A1 | 8/2017 | Johnson et al. |
| 2017/0307562 A1 | 10/2017 | Goldsmith |
| 2017/0361599 A1 | 12/2017 | Lerner et al. |
| 2017/0365474 A1 | 12/2017 | Pan et al. |
| 2017/0365477 A1 | 12/2017 | Pan et al. |
| 2017/0365562 A1 | 12/2017 | Pan et al. |
| 2018/0035932 A1 | 2/2018 | Massova |
| 2018/0037952 A1 | 2/2018 | Goldsmith |
| 2018/0037985 A1 | 2/2018 | Myers et al. |
| 2018/0110444 A1 | 4/2018 | Sherwood et al. |
| 2018/0328841 A1 | 11/2018 | Graham et al. |
| 2018/0336970 A1 | 11/2018 | Sherwood et al. |
| 2019/0025237 A1 | 1/2019 | Kelly et al. |
| 2019/0178837 A1 | 6/2019 | Xu et al. |
| 2019/0286866 A1 | 9/2019 | Gurt |
| 2020/0166435 A1 | 5/2020 | Sherwood et al. |
| 2020/0191737 A1 | 6/2020 | Sherwood et al. |
| 2021/0148848 A1 | 5/2021 | Kelly et al. |

FOREIGN PATENT DOCUMENTS

| | | |
|---|---|---|
| EP | 1764153 | 3/2007 |
| EP | 1806414 | 7/2007 |
| EP | 2542921 | 1/2013 |
| EP | 3093653 | 11/2016 |
| EP | 3431977 | 1/2019 |
| JP | H11174051 | 7/1999 |
| JP | 2011102747 W | 5/2011 |
| JP | 2016022415 | 2/2016 |
| JP | 2016122249 | 7/2016 |
| JP | 2017123912 | 7/2017 |
| WO | 9947905 | 9/1999 |
| WO | 2001070114 | 9/2001 |
| WO | 2008088780 | 7/2008 |
| WO | 2009135070 | 11/2009 |
| WO | 2013095730 | 6/2013 |
| WO | 2013189502 | 12/2013 |
| WO | 2015191558 | 12/2015 |
| WO | 2016064740 | 4/2016 |
| WO | 2016105464 | 6/2016 |
| WO | 2017218464 | 12/2017 |
| WO | 2018075731 | 4/2018 |
| WO | 2018213564 | 11/2018 |

OTHER PUBLICATIONS

Final Office Action for U.S. Appl. No. 14/883,895 dated Jul. 18, 2019 (19 pages).
Final Office Action for U.S. Appl. No. 14/883,895 dated Sep. 14, 2018 (16 pages).
International Search Report and Written Opinion for PCT Application No. PCT/US2018/033166 dated Oct. 2, 2018 (12 pages).
Tripathi, Kumud M. et al., "Recent Advances in Engineered Graphene and Composites for Detection of Volatile Organic Compounds (VOCs) and Non-Invasive Diseases Diagnosis," Carbon 110 (2016) 97-129 (34 pages).
Communication Pursuant to Article 94(3) EPC for European Patent Application No. 18180455.0 dated Feb. 11, 2019 (6 pages).
Deen, David A. et al., "Graphene-Based Quantum Capacitance Wireless Vapor Sensors," IEEE Sensors Journal, vol. 14, No. 5, May 2014 (8 pages).
Ebrish, M.A. et al., "Operation of multi-finger graphene quantum capacitance varactors using planarized local bottom gate electrodes," Applied Physics Letters, vol. 100, No. 14, Apr. 2012 (4 pages).
European Search Report for European Patent Application No. 18180455.0 dated Dec. 3, 2018 (5 pages).
First Office Action for Chinese Patent Application No. 201580056417.2 dated Feb. 11, 2019 (13 pages) with English summary.
International Preliminary Report on Patentability for PCT Application No. PCT/US2018/037144 dated Dec. 27, 2018 (7 pages).
Ma, Rui et al., "Acetone Sensing Using Graphene Quantum Capacitance Varactors," IEEE Sensors, Oct. 30, 2016 (3 pages).
Non-Final Office Action for U.S. Appl. No. 14/883,895 dated Feb. 15, 2019 (17 pages).
Opera, A. et al., "Integrated Temperature, Humidity and Gas Sensors on Flexible Substrates for Low-Power Applications," Sensors, Jan. 1, 2007 (4 pages).

(56) References Cited

OTHER PUBLICATIONS

Response to Advisory Action dated Dec. 3, 2018, for U.S. Appl. No. 14/883,895, submitted via EFS-Web on Dec. 14, 2018, 11 pages.
Response to Final Rejection dated Sep. 14, 2018, for U.S. Appl. No. 14/883,895, submitted via EFS-Web on Nov. 7, 2018, 11 pages.
Arasaradnam, R. P. et al., "Review Article: Next Generation Diagnostic Modalities in Gastroenterology—Gas Phase Volatile compund biomarker detection," Alimentary Pharmacology and Therapeutics 2014; 39: 780-789 (10 pages).
Boots, Agnes W. et al., "The Versatile Use of Exhaled Volatile Organic Compounds in Human Health and Disease," J. Breath Res. 6 (2012) 027108 (21 pages).
"Communication Pursuant to Rules 161(1) and 162 EPC," for European Patent Application No. 15790739.5 dated Jun. 1, 2017 (2 pages).
Deen, David A. et al., "Graphene-Based Quantum Capacitance Wireless Vapor Sensors," IEEE Sensors Journal, vol. 14, No. 5, May 2014,1459-1466 (8 pages).
Droscher, S. et al., "Quantum Capacitance and Density of States of Graphene," Phys. Scr. T146 (2012) 014009, pp. 1-5 (5 pages).
Ebrish, M. A. et al., "Dielectric Thickness Dependence of Quantum Capacitance in Graphene Varactors with Local Metal Back Gates," Device Research Conference, 2012 (2 pages).
"FDC1004 1-Channel Capacitance-to-Digital Converter for Capacitive Sensing Solutions," Data Sheet SNOSCY5B Texas Instruments Aug. 2014—Revised 2015 (24 pages).
"FDC1004EVM User Guide," Literature No. SNAU163C, Texas Instruments Aug. 2014—Revised Oct. 2016 (46 pages).
Fisher, James P. et al., "Central Sympathetic Overactivity: Maladies and Mechanisms," Autonomic Neuroscience 148.1 (2009): 5-15 (11 pages).
Georgakilas, Vasilios et al., "Functionalization of Graphene: Covalent and Non-Covalent Approaches, Derivatives and Applications," Chemical Reviews Nov. 14, 2012; 112(11): 59 pages.
Hu, Yuhai et al., "Chemically Functionalized Graphene and Their Applications in Electrochemical Energy Conversion and Storage," Advances in Graphene Science, Chapter 7, 2013, pp. 161-190 (30 pages).
"International Preliminary Reporton Patentability," for PCT Application No. PCT/US2015/056243 dated May 4, 2017 (8 pages).
"International Search Report and Written Opinion," for PCT Application No. PCT/US2015/056243, dated Jan. 26, 2016 (12 pages).
Koester, Steven J. "Using the Quantum Capacitance in Graphene to Enable Varactors for Passive Wireless Sensing Applications," 2011 IEEE Sensors Proceedings, pp. 994-997, 2011 (4 pages).
Li, Xiao et al., "Digital Health: Tracking Physiomes and Activity Using Wearable Biosensors Reveals Useful Health-Related Information," PLoS Biology 15.1 (2017): e2001402 (30 pages).
"Mechanical Data," DGS (S-PDSO-G10) DSC0010B Package Outline, Example Board Layout, and Stencil Design. Texas Instruments 2016 (5 pages).
Nakhleh, Morad K. et al., "Diagnosis and Classification of 17 Diseases from 1404 Subjects via Pattern Analysis of Exhaled Molecules," ACS Nano 2017, 11, 112-125 (14 pages).
"Nano Mobile Healthcare Inc.," Company Profile on Reuters.com URL <http://www.renters.com/finance/stocks/companyProfile?symbol=VNTH.PK> accessed Mar. 17, 2017 (2 pages).
"Package Materials Information," Tape and Reel Information and Box Dimensions. Texas Instruments Feb. 13, 2016 (2 pages).
"Package Option Addendum," Packaging Information for FDC1004DGSR, DGST, DSCJ, DSCR and DSCT Devices. Texas Instruments May 2015 (2 pages).
"Standard Terms and Conditions for Evaluation Modules," Texas Instruments 2016 (5 pages).
Wang, David "FDC1004: Basics of Capacitive Sensing and Applications," Application Report SNOA927, Texas Instruments Dec. 2014 (12 pages).
Non-Final Office Action for U.S. Appl. No. 15/787,985 dated Oct. 10, 2019 (40 pages).
Response to Advisory Action dated Oct. 11, 2019 for U.S. Appl. No. 14/883,895, submitted via EFS-Web on Oct. 16, 2019, 10 pages.
Response to Communication Pursuant to Article 94(3) EPC for European Patent Application No. 18180455.0 filed Nov. 12, 2019 (9 pages).
Response to Final Rejection dated Jul. 18, 2019 for U.S. Appl. No. 14/883,895, submitted via EFS-Web on Sep. 18, 2019, 10 pages.
Second Office Action for Chinese Patent Application No. 201580056417.2 dated Sep. 25, 2019 (6 pages) No English Translation.
Ebrish, M. A. et al., "Operation of Multi-Finger Graphene Quantum Capacitance Varactors using Planarized Local Bottom Gate Electrodes," Applied Physics Letters, A I P Publishing LLC, 2012 (5 pages).
European Search Report for Dutch Patent Application No. 2019492 dated Apr. 12, 2018 (10 pages).
International Search Report and Written Opinion for PCT Application No. PCT/US2017/037144 dated Oct. 6, 2017 (11 pages).
International Search Report and Written Opinion for PCT Application No. PCT/US2017/057318 dated Feb. 6, 2018 (14 pages).
Ma, Rui et al., "Acetone Sensing Using Graphene Quantum Capacitance Varactors," 2016 IEEE Sensors, Orlando, FL, 2016 (3 pages).
Non-Final Office Action for U.S. Appl. No. 14/883,895 dated Apr. 30, 2018 (37 pages).
Oprea, A. et al., "Integrated Temperature, Humidity and Gas Sensors on Flexible Substrates for Low-Power Applications," 007 IEEE Sensors, Atlanta, GA, 2007, pp. 158-161 (4 pages).
Response to Communication Pursuant to Rules 161 (1) and 162 EPC for European Patent Application No. 15790739.5 filed with the EPO on Dec. 8, 2017 (14 pages).
Response to Non-Final Office Action for U.S. Appl. No. 14/883,895, dated Apr. 30, 2018 and filed with the USPTO Jul. 2, 2018 (18 pages).
International Preliminary Report on Patentability for PCT Application No. PCT/US2017/057318 dated May 2, 2019 (11 pages).
Response to Communication Pursuant to Article 94(3) EPC for European Patent Application No. 18180455.0 filed Jun. 6, 2019 (44 pages).
Response to Communication Pursuant to Rules 161 (1) and 162 EPC for European Patent Application No. 17733246.7 filed May 29, 2019 (22 pages).
Response to Non-Final Rejection dated Feb. 15, 2019 for U.S. Appl. No. 14/883,895, submitted via EFS-Web on May 10, 2019, 10 pages.
Bhadra, Sharmista et al., "Non-destructive detection offish spoilage using a wireless basic volatile sensor," Taianta, vol. 134, Dec. 25, 2014 pp. 718-723 (6 pages).
Communication Pursuant to Article 94(3) EPC for European Patent Application No. 15790739.5 dated Dec. 17, 2019 (5 pages).
Communication Pursuant to Article 94(3) EPC for European Patent Application No. 18180455.0 dated Dec. 20, 2019 (3 pages).
Ebrish, Mona A. et al., "Effect of Noncovalent Basal Plane Functionalization of the Quantum Capacitance in Graphene," ACS Appl. Mater. Interfaces 2014, 6, 10296-10303 (8 pages).
Final Office Action for U.S. Appl. No. 14/883,895 dated May 1, 2020 (19 pages).
Final Office Action for U.S. Appl. No. 15/787,985 dated Jan. 17, 2020 (16 pages).
International Preliminary Report on Patentability for PCT Application No. PCT/US2018/033166 dated Nov. 28, 2019 (8 pages).
International Search Report and Written Opinion for PCT Application No. PCT/US2019/063324 dated Mar. 27, 2020 (17 pages).
International Search Report and Written Opinion for PCT Application No. PCT/US2019/065981 dated Mar. 16, 2020 (14 pages).
Koester, Steven J. "High Quality Factor Graphene Varactors for Wireless Sensing Applications," Applied Physics Letters 99, 163105 (2011), 3 pages.
Navaneethan, Udayakumar et al., "Volatile Organic Compounds in Bile Can Diagnose Malignant Biliary Strictures in the Setting of Pancreatic Cancer: A Preliminary Observation," Gastrointest Endosc. Dec. 2014;80(6):1038-45 (8 pages).
Non-Final Office Action for U.S. Appl. No. 14/883,895 dated Nov. 27, 2019 (16 pages).

(56) References Cited

OTHER PUBLICATIONS

Non-Final Office Action for U.S. Appl. No. 15/982,506 dated Dec. 11, 2019 (41 pages).
Non-Final Office Action for U.S. Appl. No. 16/037,218 dated Apr. 29, 2020 (46 pages).
Notice of Allowance for U.S. Appl. No. 15/982,506 dated May 7, 2020 (17 pages).
Office Action for Japanese Patent Application No. 2019-517196 dated Feb. 4, 2020 (10 pages) with English Translation.
Olson, Eric J. et al., "Capacitive Sensing of Intercalated H2O Molecules Using Graphene," ACS Appl. Mater. Interfaces 2015, 7(46), 25804-25812 (29 pages).
Response to Communication Pursuant to Article 94(3) EPC for European Patent Application No. 15790739.5 filed Apr. 24, 2020 (16 pages).
Response to Communication Pursuant to Article 94(3) EPC for European Patent Application No. 18180455.0 filed Apr. 21, 2020 (24 pages).
Response to Communication Pursuant to Rules 161(1) and 162 EPC for European Patent Application No. 17794832.0 filed Dec. 6, 2019 (9 pages).
Response to Final Rejection dated Jan. 17, 2020 for U.S. Appl. No. 15/787,985, submitted via EFS-Web on Apr. 9, 2020, 12 pages.
Response to Non-Final Rejection dated Dec. 11, 2019 for U.S. Appl. No. 15/982,506, submitted via EFS-Web on Feb. 25, 2020, 13 pages.
Response to Non-Final Rejection dated Nov. 27, 2019 for U.S. Appl. No. 14/883,895 submitted via EFS-Web on Feb. 5, 2020, 9 pages.
Response to Non-Final Rejection dated Oct. 10, 2019 for U.S. Appl. No. 15/787,985, submitted via EFS-Web on Jan. 7, 2020, 17 pages.
Third Office Action for Chinese Patent Application No. 201580056417.2 dated Feb. 18, 2020 (6 pages) No English Translation.
Zhang, Yao et al., "Capacitive Sensing of Glucose in Electrolytes using Graphene Quantum Capacitance Varactors," ACS Appl. Mater. Interfaces 2017, 9, 38863-38869 (7 pages).
Zhang, Yao et al., "Glucose Sensing with Graphene Varactors," IEEE Sensors, Sensors 2016—Proceedings, Orlando, FL 2016 (3 pages).
Zhen, Xue et al., "Noncovalent Monolayer Modification of Graphene Using Pyrene and Cyclodextrin Receptors for Chemical Sensing," ACS Applied Nano Materials 2018, vol. 1, No. 6 pp. 2718-2726 (9 pages).
Non-Final Office Action for U.S. Appl. No. 15/787,985 dated Jun. 29, 2020 (14 pages).
Notice of Allowance for U.S. Appl. No. 16/037,218 dated Jul. 31, 2020 (20 pages).
Office Action for Japanese Patent Application No. 2019-520955 dated Jul. 14, 2020 (10 pages) with English Translation.
Response to Communication Pursuant to Rules 161(1) and 162 EPC for European Patent Application No. 18731579.1 filed Jul. 17, 2020 (19 pages).
Response to Final Rejection dated May 1, 2020 for U.S. Appl. No. 14/883,895, submitted via EFS-Web on Jul. 15, 2020, 12 pages.
Response to Non-Final Rejection dated Apr. 29, 2020 for U.S. Appl. No. 16/037,218, submitted via EFS-Web on Jul. 15, 2020, 7 pages.
Response to Non-Final Rejection dated Jun. 29, 2020 for U.S. Appl. No. 15/787,985, submitted via EFS-Web on Sep. 29, 2020, 9 pages.
Communication Pursuant to Article 94(3) EPC for European Patent Application No. 18731579.1 dated Nov. 10, 2020 (5 pages).
Final Office Action for U.S. Appl. No. 15/787,985 dated Oct. 21, 2020 (21 pages).
First Office Action for Chinese Patent Application No. 201780030595.7 dated Nov. 2, 2020 (12 pages) with English Summary.
Office Action for Japanese Patent Application No. 2019-563876 dated Nov. 4, 2020 (3 pages) No English Translation.
Response to Final Rejection dated Oct. 21, 2020 for U.S. Appl. No. 15/787,985, submitted via EFS-Web on Jan. 21, 2021, 8 pages.
"Extended European Search Report," for European Patent Application No. 20214733.6 dated Apr. 21, 2021 (11 pages).
"Non-Final Office Action," for U.S. Appl. No. 15/787,985 dated Apr. 16, 2021 (16 pages).
"Office Action," for Japanese Patent Application No. 2019-520955 dated Feb. 9, 2021 (11 pages) with English Translation.
"Response to Communication Pursuant to Article 94(3) EPC," for European Patent Application No. 18731579.1 filed Mar. 15, 2021 (12 pages).
Zhang, Xu et al., "A Wide Measurement Range and Fast Update Rate Integrated Interface for Capacitive Sensors Array," IEEE Transactions on Circuits and Systems-1: Regular Papers, Vo. 61, No. 1, Jan. 2014, pp. 2-11 (10 pages).
"International Preliminary Report on Patentability," for PCT Application No. PCT/US2019/063324 dated Jun. 10, 2021 (10 pages).
"Non-Final Office Action," for U.S. Appl. No. 14/883,895 dated May 20, 2021 (34 pages).
"Office Action," for Chinese Patent Application No. 201780065376.2 dated Apr. 27, 2021 (10 pages) with English Summary.
Second Office Action for Chinese Patent Application No. 201780030595.7 dated Jun. 17, 2021 (8 pages).
"International Preliminary Report on Patentability," for PCT Application No. PCT/US2019/065981 dated Jul. 1, 2021 (8 pages).
"Summons to attend oral proceedings pursuant to Rule 115(1) EPC," for European Patent Application No. 18731579.1 dated Jul. 1, 2021 (6 pages).

* cited by examiner ced. Diseases can be detected using many different
GAS SAMPLING CATHETERS, SYSTEMS AND METHODS This application claims the benefit of U.S. Provisional Application No. 62/350,345, filed Jun. 15, 2016, the contents of which are herein incorporated by reference.

FIELD

Embodiments herein relate to gas sampling catheters, systems and related methods.

BACKGROUND

The accurate detection of diseases can allow clinicians to provide appropriate therapeutic interventions. Further, the early detection of diseases can lead to better treatment outcomes. Diseases can be detected using many different techniques including analyzing tissue samples, analyzing various bodily fluids, diagnostic scans, and the like.

Some disease states result in the increased or decreased production of specific chemical compounds. As such, the detection of these chemical compounds in gas samples or patterns of the same can allow for the early detection of particular disease states.

SUMMARY

Embodiments herein include gas sampling catheters, systems and related methods. In an example, a gas sampling catheter is included. The catheter can include a catheter shaft having a proximal end and a distal end, the catheter shaft defining a lumen therein. The catheter can also include a gas sampling port providing fluid communication between the exterior of the catheter shaft adjacent the distal end of the lumen of the catheter shaft. The catheter can further include a sensor element disposed in fluid communication with the lumen, the sensor element configured to detect a component of a gaseous sample. The sensor element can include a first measurement zone comprising a plurality of discrete binding detectors.

In addition, in some examples, the gas sampling catheter can further include a filter element disposed in a path of fluid flow between the gas sampling port and the sensor element. In addition, the filter element can include electrospun filter media in some examples. In addition to, or in the alternative, in some examples the gas sampling catheter can include a porous membrane disposed in a path of fluid flow between the gas sampling port and the sensor element. In some examples, the porous membrane can include an expanded polytetrafluoroethylene membrane. In addition to, or in the alternative, the gas sampling catheter can further include a second gas sampling port providing fluid communication between the exterior of the catheter shaft and the lumen of the catheter shaft at a position adjacent the distal end of catheter shaft.

In addition to, or in the alternative, the gas sampling catheter can include a manifold structure in fluid communication with the gas sampling port, the manifold structure defining a plurality of gas flow paths. In addition to, or in the alternative, the gas sampling catheter can include a plurality of filter elements in fluid communication with the plurality of gas flow paths of the manifold. In addition to, or in the alternative, the gas sampling catheter can include a plurality of sensor elements in fluid communication with the plurality of gas flow paths of the manifold. In addition to, or in the alternative, the gas sampling catheter can include a plurality of sensor elements disposed serially within the lumen of the catheter shaft. In addition to, or in the alternative, the gas sampling catheter can include a plurality of filter elements disposed serially within the lumen of the catheter shaft.

In addition to, or in the alternative, the gas sampling catheter can include a vacuum generator in fluid communication with the proximal end of the catheter shaft lumen. In addition to, or in the alternative, the gas sampling catheter can include a valve to control fluid communication between the vacuum generator and the catheter shaft lumen. In addition to, or in the alternative, the gas sampling catheter can include one or more electronic alignment elements disposed along the catheter shaft. In some examples, the one or more electronic alignment elements are indicative of the position of one or more sensor elements. In addition to, or in the alternative, the gas sampling catheter can include one or more external indicia disposed along the exterior of the catheter shaft. In some examples, the one or more external indicia are indicative of the position of one or more sensor elements. In addition to, or in the alternative, the gas sampling catheter can be disposable.

In addition to, or in the alternative, the gas sampling catheter can include a first measurement zone defining a portion of a first gas flow path, the sensor element further comprising a second measurement zone, separate from the first measurement zone, the second measurement zone comprising a plurality of discrete binding detectors, the second measurement zone disposed outside of the first gas flow path. In some examples, the discrete binding detectors each comprising an LRC resonator circuit.

In some examples, the sensor element is disposed within the lumen at a position that remains outside of the patient. In some examples, the sensor element is disposed within a housing that is in fluid communication with the lumen of the gas sampling catheter. In some examples, the sensor element is disposed within the lumen at a position that is inside of the patient when a gas sample is drawn.

In an embodiment, an apparatus for sampling gases in a patient is included. The apparatus can include a device such as an endoscope or a bronchoscope or other similar device, the device comprising a lumen. The apparatus can further include a gas sampling catheter disposed within a lumen of the device. The gas sampling catheter can include a catheter shaft having a proximal end and a distal end, the catheter shaft defining a lumen therein. The catheter can further include a gas sampling port providing fluid communication between the exterior of the catheter shaft adjacent the distal end of the lumen of the catheter shaft. The catheter can further include a sensor element disposed within the lumen, the sensor element configured to detect a component of a gaseous sample. The sensor element can include a first measurement zone comprising a plurality of discrete binding detectors.

In an embodiment, a method for sampling a gas of a patient is included. The method can include inserting a disposable gas sampling catheter into a patient, drawing in a fluid sample of the patient into gas sampling catheter and contacting the fluid sample with a sensor element disposed within the lumen, the sensor element configured to detect a component of a gaseous sample. The sensor element can include a first measurement zone comprising a plurality of discrete binding detectors.

In addition, or in the alternative, the method can further include withdrawing the disposable gas sampling catheter from the patient. In addition, or in the alternative, the method can further include gathering data from the plurality of discrete binding detectors. In addition, or in the alternative, the method can further include wirelessly gathering data from the plurality of discrete binding detectors. In addition, or in the alternative, the data can be gathered prior to withdrawing the disposable gas sampling catheter from the patient. In addition, or in the alternative, the data can be gathered after withdrawing the disposable gas sampling catheter from the patient.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following drawings, in which.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

The embodiments described herein are not intended to be exhaustive or to limit the invention to the precise forms disclosed in the following detailed description. Rather, the embodiments are chosen and described so that others skilled in the art can appreciate and understand the principles and practices.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

As described above, some disease states result in increased or decreased production of specific chemical compounds. The detection of these chemical compounds in gas samples, or patterns of such chemical compounds, can allow for the early detection of particular disease states. However, obtaining gas samples for testing can be challenging. In some cases, if a gas sample must pass through different parts of a patient's anatomy while being exposed to local environments during passage, the composition of the gas sample can be changed hindering diagnostic use of the sample.

Embodiments herein relate to gas sampling catheters, systems including the same, and related methods. The gas sampling catheters herein can be at least partially introduced into the anatomy of a patient in order to collect gas samples for analysis. In various embodiments, the gas sampling catheters can include one or more sensor elements disposed in fluid communication with a lumen of the catheter. The sensor element can be configured to detect a component of a gaseous sample. In some embodiments, the sensor element can be physically disposed within the gas sampling catheter. In other embodiments, the sensor element can be outside of the catheter but in fluid communication with a lumen of the catheter.

Figure 1:
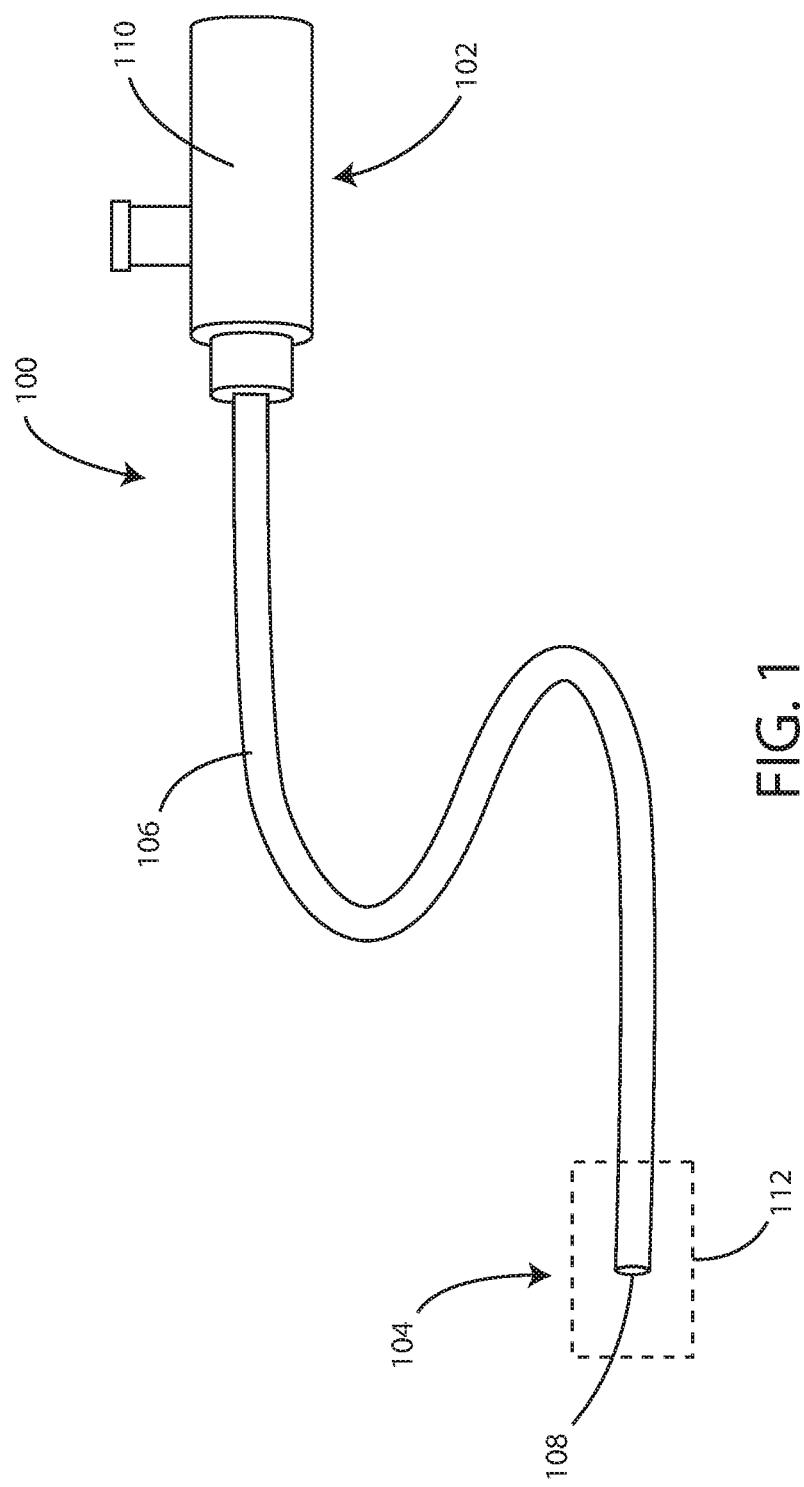
FIG. 1 is a schematic view of a gas sampling catheter in accordance with various embodiments herein.

Referring now to FIG. 1, a schematic view of a gas sampling catheter 100 is shown in accordance with various embodiments herein. The catheter 100 includes a catheter shaft 106 and has a proximal end 102 and distal end 104. The catheter shaft can define a gas flow path there through (not shown in this view). The catheter 100 can include a housing 110 (or proximal housing) disposed on the proximal end 102. The housing 110 can be in fluid communication with the gas flow path within the housing 110. The catheter 100 can also include a gas sampling port 108 on the distal end 104.

Figure 2:
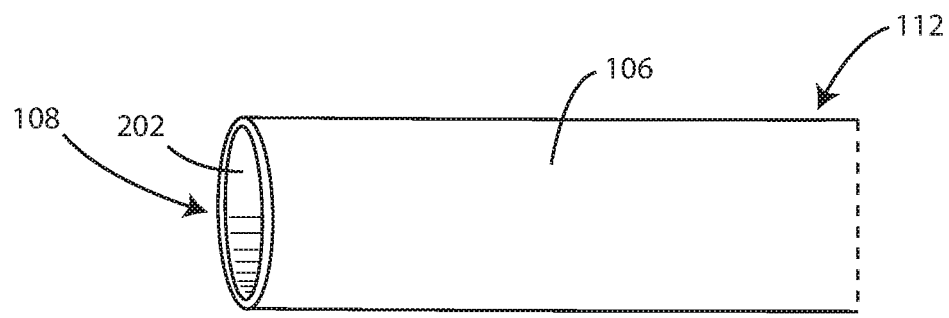
FIG. 2 is a schematic view of a distal portion of a gas sampling catheter in accordance with various embodiments herein.
Figure 3:
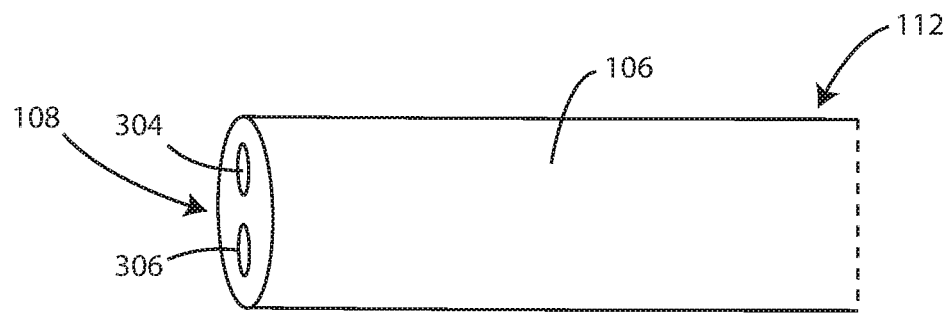
FIG. 3 is a schematic view of a distal portion of a gas sampling catheter in accordance with various embodiments herein.
Figure 4:
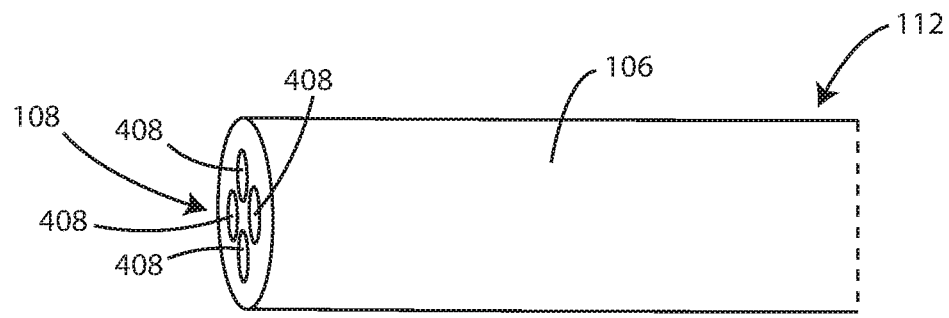
FIG. 4 is a schematic view of a distal portion of a gas sampling catheter in accordance with various embodiments herein.

Referring now to FIG. 2, a schematic view of a distal portion 112 of a gas sampling catheter is shown in accordance with various embodiments herein. The distal portion 112 of the catheter can include an aperture 202 which serves as the gas sampling port 108. However, in some embodiments, the gas sampling port 108 can include multiple apertures. The multiple apertures can be in communication with the same gas flow path or can be in fluid communication with separate gas flow paths. Referring now to FIG. 3, a schematic view of a distal portion 112 of a gas sampling catheter is shown in accordance with various embodiments herein. In this example, the gas sampling port 108 includes a first aperture 304 and a second aperture 306. Referring now to FIG. 4, a schematic view of a distal portion 112 of a gas sampling catheter is shown in accordance with various embodiments herein. In this example, the gas sampling port 108 includes four apertures 408. While in the examples of FIGS. 2-4, the apertures have been disposed on the very end of the catheter, it will be appreciated that the aperture can be disposed in other locations. For example, in some embodiments, one or more of the apertures can be disposed on the sides of the catheter shaft.

Figure 5:
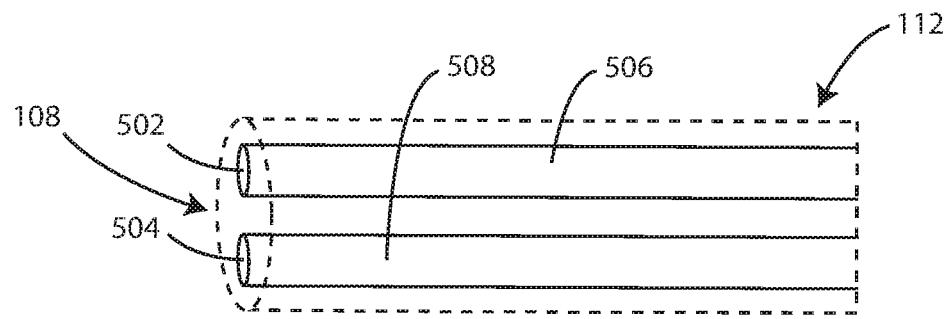
FIG. 5 is a schematic view showing gas flow paths in a portion of a gas sampling catheter in accordance with various embodiments herein.

In some cases, the catheter can define a single gas flow path there through. In other embodiments, the catheter can define multiple distinct gas flow paths. In some cases, different gas flow paths can be interconnected, such as through a manifold structure. Referring now to FIG. 5, a schematic view is shown of gas flow paths in a portion 112 of a gas sampling catheter in accordance with various embodiments herein. The gas sampling catheter can include a gas sampling port 108 including a first aperture 502 and a second aperture 504. The first aperture 502 can be in fluid communication with the first gas flow path 506. The second aperture 504 can be in fluid communication with a second gas flow path 508.

Figure 6:
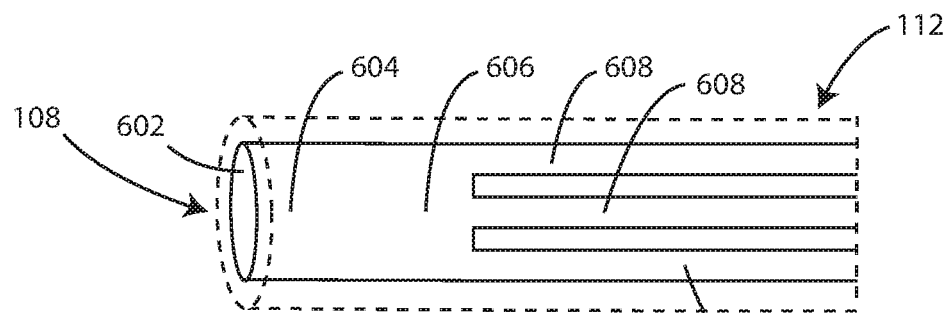
FIG. 6 is a schematic view showing gas flow paths in a portion of a gas sampling catheter in accordance with various embodiments herein.

Referring now to FIG. 6, a schematic view is shown of gas flow paths in a portion 112 of a gas sampling catheter in accordance with various embodiments herein. In this example, the gas sampling catheter can include a gas sampling port 108 including a single aperture 602. The aperture 602 can be in fluid communication with a combined gas flow 604 which is in fluid communication with a manifold structure 606. The manifold structure 606 can be in fluid communication with gas flow paths 608.

Figure 7:
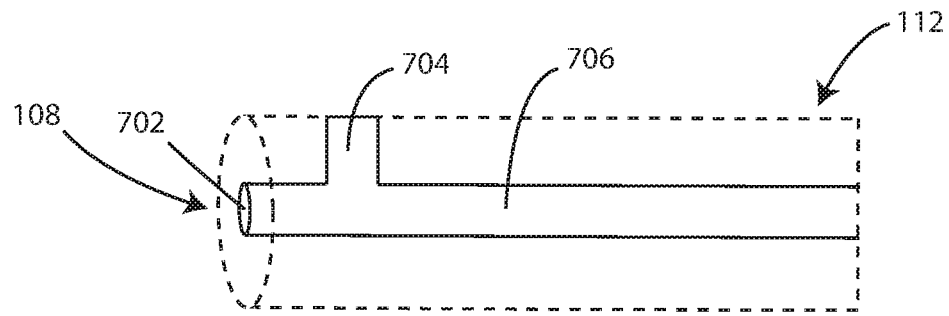
FIG. 7 is a schematic view showing gas flow paths in a portion of a gas sampling catheter in accordance with various embodiments herein.

Referring now to FIG. 7, a schematic view is shown of gas flow paths in a portion 112 of a gas sampling catheter in accordance with various embodiments herein. In this example, the gas sampling port 108 can include a first aperture 702 disposed on the end of the catheter and a second aperture 704 disposed on the side of the catheter. In this example, both the first aperture 702 and the second aperture 704 can be connected together and in fluid communication with a common gas flow path 706. However, in other embodiments, the first aperture 702 and the second aperture 704 can be in fluid communication with separate gas flow paths.

Figure 8:
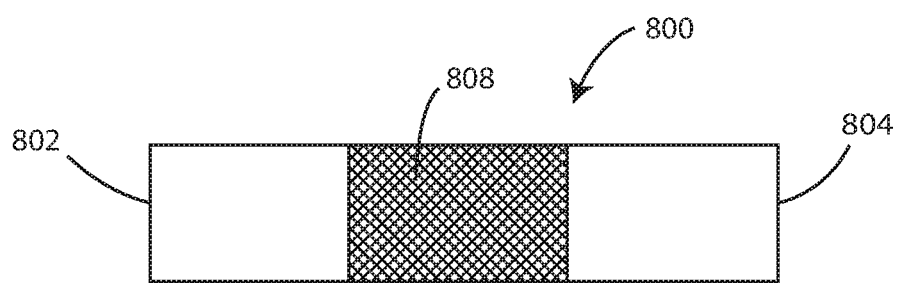
FIG. 8 is a schematic view showing elements within a gas flow path of a gas sampling catheter in accordance with various embodiments herein.

Referring now to FIG. 8, a schematic view is shown of elements within a gas flow path 800 of a gas sampling catheter in accordance with various embodiments herein. In this view, the gas flow path 800 includes an upstream side 802 (side for gas ingress) and a downstream side 804 (side for gas egress). A sensor element 808 can be disposed within the gas flow path 800. The sensor element 808 can be disposed in fluid communication with a lumen of the catheter. The sensor element 808 can be configured to detect a component of a gaseous sample. The sensor element can include a first measurement zone comprising a plurality of discrete binding detectors. Aspects of sensor elements are described in greater detail below.

Figure 9:
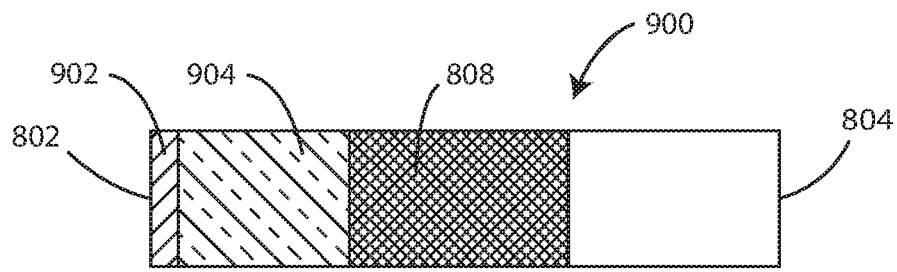
FIG. 9 is a schematic view showing elements within a gas flow path of a gas sampling catheter in accordance with various embodiments herein.

Referring now to FIG. 9, a schematic view is shown of elements within a gas flow path 900 of a gas sampling catheter in accordance with various embodiments herein. A porous membrane 902 can be disposed in the gas flow path 900 along with a filter element 904, and a sensor element 808. The filter element 904 can include electrospun filter media. Further aspects of exemplary filter elements are described in greater detail below. The porous membrane 902 can be disposed in a path of fluid flow between the gas sampling port and the sensor element 808. The porous membrane 902 can be an expanded polytetrafluoroethylene membrane. In some embodiments, the gas sampling catheter can include the filter element, but not the porous membrane. In some embodiments, the gas sampling catheter can include the porous membrane but not the filter element.

Figure 10:
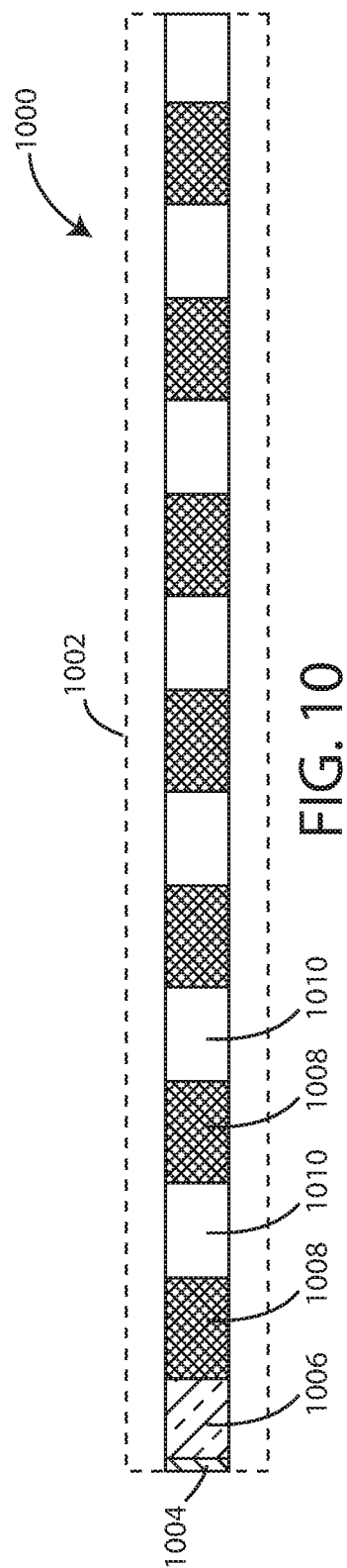
FIG. 10 is a schematic view showing elements of a gas sampling catheter in accordance with various embodiments herein.

In some embodiments, the gas sampling catheter can include a plurality of sensor elements disposed in series with one another. Referring now to FIG. 10, a schematic view is shown of elements of a gas sampling catheter 1000 in accordance with various embodiments herein. A catheter shaft 1002 can include a lumen therein. The lumen can define a gas flow path. In some embodiments, the catheter 1000 can include a porous membrane 1004 and a filter element 1006. A plurality of sensor elements 1008 can be disposed within the catheter 1000. The sensor elements 1008 can be separated by a series of gaps 1010 disposed there between. However, in other embodiments, there are no gaps between the sensor elements. In some embodiments the gaps can be approximately equal in size. In other embodiments, some of the gaps are larger than others. In some embodiments the gaps closer toward the distal end are small than toward the proximal end of the catheter.

Figure 11:
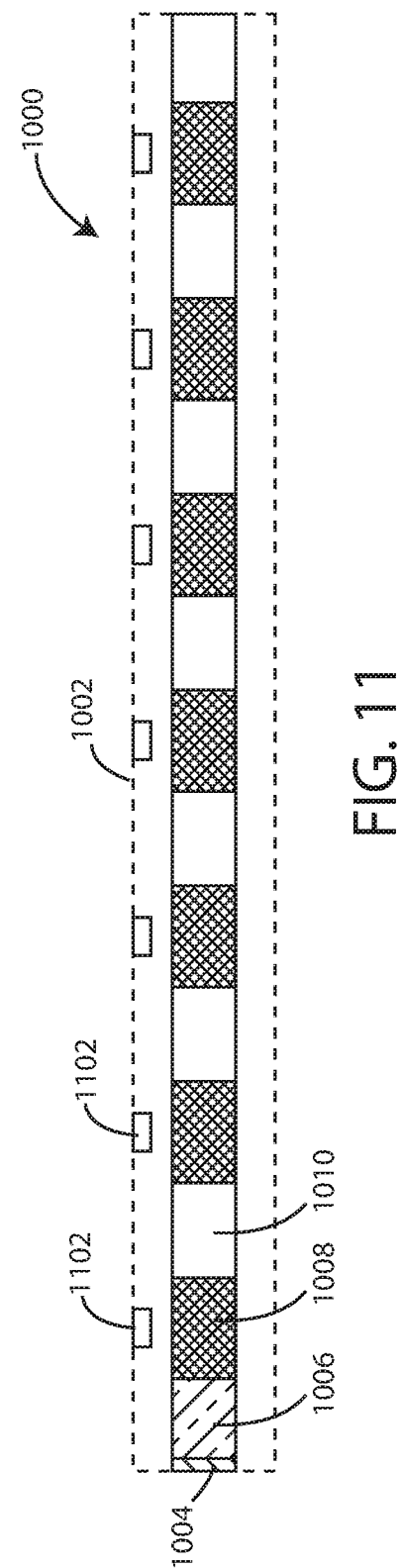
FIG. 11 is a schematic view showing elements of a gas sampling catheter in accordance with various embodiments herein.

In some embodiments, alignment elements, such as magnets or other types of markers that can be detected are disposed along the catheter shaft. For example, if the sensor elements of the catheter are read (e.g., interrogated to gather data) by a different device, then the alignment elements can be used to ensure that the catheter is properly aligned with the reading device. The sensor elements may be interrogated in various ways. In some embodiments, the sensor elements may be evaluated using a wireless approach, such as using radiofrequency methods. In other embodiments, the sensor elements may be interrogated through a direct electrical connection to a reading device, such as via electrical contacts on the catheter. Referring now to FIG. 11, a schematic view is shown of elements of a gas sampling catheter 1000 in accordance with various embodiments herein. The catheter shaft 1002 can include a lumen therein. The lumen can define a gas flow path. In some embodiments, the catheter 1000 can include a porous membrane 1004 and a filter element 1006. A plurality of sensor elements 1008 can be disposed within the catheter 1000. The sensor elements 1008 can be separated by a series of gaps 1010 disposed there between. The catheter 1000 can further include alignment elements 1102. The alignment elements 1102 align with the positions of the sensor elements 1008. In this manner, detection of the alignment elements 1102 can allow detection of the position of the sensor elements for purposes of gathering data from the sensor elements or for other purposes.

Figure 12:
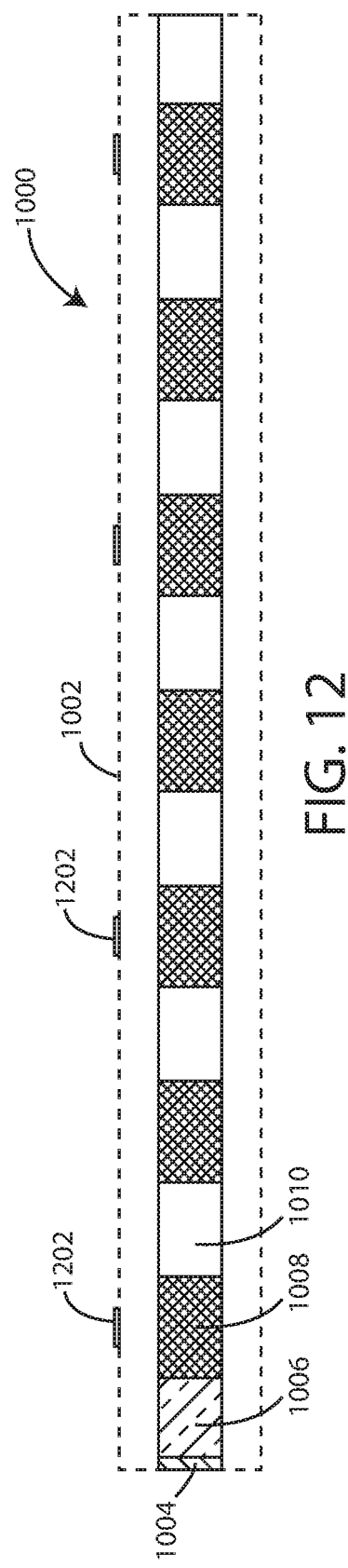
FIG. 12 is a schematic view showing elements of a gas sampling catheter in accordance with various embodiments herein.

In some embodiments, indicia disposed on the catheter shaft can be used to indicate the position of the sensor elements. Referring now to FIG. 12, a schematic view is shown of elements of a gas sampling catheter 1000 in accordance with various embodiments herein. The catheter shaft 1002 can include a lumen therein. The lumen can define a gas flow path. In some embodiments, the catheter 1000 can include a porous membrane 1004 and a filter element 1006. A plurality of sensor elements 1008 can be disposed within the catheter 1000. The sensor elements 1008 can be separated by a series of gaps 1010 disposed there between. The catheter 1000 can further include indicia 1202. The indicia 1202 can align with at least some of the sensor elements 1008 so as to indicate their position within the catheter shaft.

Figure 13:
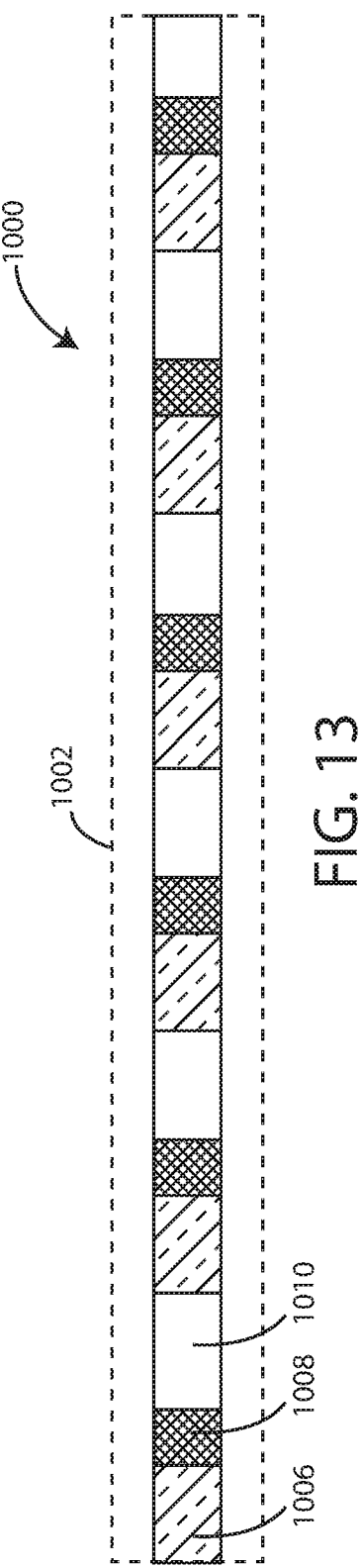
FIG. 13 is a schematic view showing elements of a gas sampling catheter in accordance with various embodiments herein.

In some embodiments, multiple filter elements can be disposed within the catheter. In some embodiments, the filter elements can all be the same. In other embodiments, the filter elements can be different from one another. In some embodiments, the filter elements can have more or less affinity for certain molecules and therefor enrich (relatively) a gas sample in some components or deplete certain components from a gas sample. Referring now to FIG. 13, a schematic view is shown of elements of a gas sampling catheter 1000 in accordance with various embodiments herein. The catheter shaft 1002 can include a lumen therein. The lumen can define a gas flow path. A plurality of filter element 1006 can be disposed within the catheter 1000. A plurality of sensor elements 1008 can also be disposed within the catheter 1000. The sensor elements 1008 can be separated by a series of gaps 1010 disposed there between.

Filter elements can be formed of various materials and can have various different structural configurations. Filter elements can include materials that adsorb or absorb components within a gas sample producing a filtered gas sample. Filter element materials (filter media) can include, but are not limited to, natural materials, synthetic materials, polymers, glasses, metals, ceramics, proteins, carbohydrates, carbon and the like. Filter element materials can be in the form of particles, fibers, webs, matrices, porous solids and the like. Binding materials can be disposed within filter elements having affinity for certain types of molecules allowing those molecules to be selectively depleted from the gas sample. In some embodiments, a filter structure can be produced through an electrospinning process. Electrospun materials can specifically include electrospun polymeric fibers.

Figure 14:
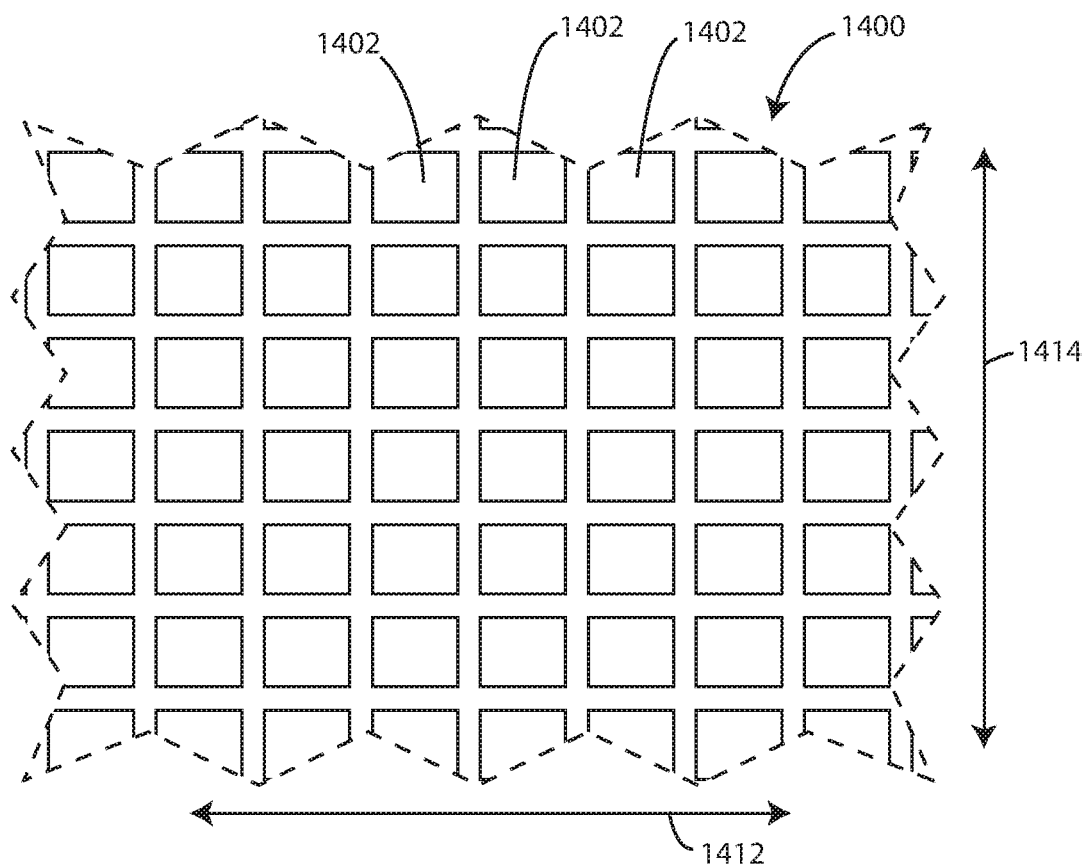
FIG. 14 is a schematic diagram of a portion of a measurement zone in accordance with various embodiments herein.

Sensor elements herein can include one or more measurement zones. Each measurement zone can include discrete binding detectors. Referring now to FIG. 14, a schematic diagram of a portion of a measurement zone 1400 is shown in accordance with various embodiments herein. A plurality of discrete binding detectors 1402 can be disposed within the measurement zone 1400. In some embodiments, the discrete binding detectors can be heterogeneous in that they are all different from one another in terms of their binding behavior or specificity with regard to analytes. In some embodiments, some discrete binding detectors can be duplicated for validation purposes, but are otherwise heterogeneous from other discrete binding detectors. While the discrete binding detectors 1402 of FIG. 14 are shown as boxes organized into a grid, it will be appreciated that the discrete binding detectors can take on many different shapes (including, but not limited to, various polygons, circles, ovals, irregular shapes, and the like) and, in turn, the groups of discrete binding detectors can be arranged into many different patterns (including, but not limited to, star patterns, zig-zag patterns, radial patterns, symbolic patterns, and the like).

In some embodiments, the order of specific discrete binding detectors 1402 across the length 1412 and width 1414 of the measurement zone can be substantially random. In other embodiments, the order can be specific. For example, in some embodiments, a measurement zone can be ordered so that the specific discrete binding detectors 1402 for analytes having a lower molecular weight are located farther away from the incoming gas flow relative to specific discrete binding detectors 1402 for analytes having a higher molecular weight which are located closer to the incoming gas flow. As such, chromatographic effects which may serve to provide separation between chemical compounds of different molecular weight can be taken advantage of to provide for optimal binding of chemical compounds to corresponding discrete binding detectors.

In some embodiments, a measurement zone can be ordered so that the specific discrete binding detectors 1402 for analytes having a lower polarity are located a farther distance from the incoming gas flow and specific discrete binding detectors 1402 for analytes having a higher polarity are located closer to the incoming gas flow. Alternately, the discrete binding detectors 1402 can be ordered in the opposite manner. In this way, an electric field can be applied near the measurement zones such that the gas samples flow through the electric field and effectively concentrate analytes from the gas samples in the area where the corresponding discrete binding detectors are located.

The number of discrete binding detectors 1402 within a particular measurement zone can be from about 1 to about 100,000. In some embodiments, the number of discrete binding detectors 1402 can be from about 1 to about 10,000. In some embodiments, the number of discrete binding detectors 1402 can be from about 1 to about 1,000. In some embodiments, the number of discrete binding detectors can be from about 2 to about 500. In some embodiments, the number of discrete binding detectors can be from about 10 to about 500. In some embodiments, the number of discrete binding detectors can be from about 50 to about 500. In some embodiments, the number of discrete binding detectors can be from about 1 to about 250.

Each of the discrete binding detectors 1402 can include at least a portion of one or more electrical circuits. By way of example, in some embodiments, each of the discrete binding detectors can include one or more passive electrical circuits. The electrical properties of the electrical circuit can change upon binding, such as specific and/or non-specific binding, with a component from a gas sample.

The discrete binding detectors can be functionalized with analyte binding receptors capable of specific binding and/or analyte binding receptors capable of non-specific binding. It will be appreciated that there are various chemistries which can be utilized to facilitate attachment of analyte binding receptors. By way of example, in the context of attachment to a graphene surface, covalent or non-covalent binding approaches can be used. Covalent binding approaches can include the formation of covalent bonds between free radicals or dienophiles of molecules to be attached or intermediates and C=C bonds of graphene layers. Covalent binding approaches can also include the formation of covalent bonds between organic functional groups of molecules to be attached or intermediates and oxygen groups of graphene oxide (a graphene derivative). As just one example, a diazonium salt can be heated producing a highly reactive free radical which attacks the $sp^2$ carbon atoms of graphene forming a covalent bond. The diazonium salt itself can be modified to contain the desired functional group(s) with which the graphene is functionalized or can include linking groups to which other desired functional group(s) can later be attached.

Various approaches to the functionalization of graphene are described in Georgakilas et al., *Functionalization of Graphene: Covalent and Non-Covalent Approaches, Derivatives and Applications*, Chemical Reviews, 2012 Nov. 14; 112(11):6156-214; U.S. Publ. Appl. No. 2011/0017587; and U.S. Publ. Appl. No. 2014/0275597, the content of all of which is herein incorporated by reference. Functionalization approaches can include, but are not limited to, polymeric thin films, metal oxide particles, and the like.

It will be appreciated that there are various structures that can be used as analyte binding receptors. Exemplary structures for binding can include, but are not limited to, antibodies, antibody fragments, nonimmuno-proteins, nucleic acids, other organic receptors, small molecule receptors, inorganic receptors, and the like.

Each particular discrete binding detector can include one or more analyte binding receptors bound thereto. In some embodiments, all of the analyte binding receptors within a particular discrete binding detector can be the same with respect to their analyte binding properties. In other embodiments, at least some of the analyte binding receptors within a particular zone can be different from one another with respect to their analyte binding properties. In some embodiments, each discrete binding detector can be unique. In some embodiments, discrete binding detectors that are unique can be cross-reactive in that they bind to different portions or different configurations of the same chemical compound. In some embodiments, each discrete binding detector can include a single passive sensor circuit. In other embodiments, each discrete binding detector can include multiple passive sensor circuits.

Figure 15:
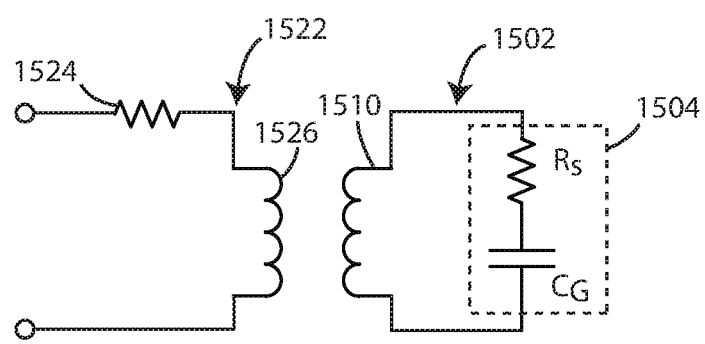
FIG. 15 is a circuit diagram of a passive sensor circuit and a portion of a reading circuit is shown in accordance with various embodiments herein.

Referring now to FIG. 15, a schematic diagram of a passive sensor circuit 1502 and a portion of a reading circuit 1522 is shown in accordance with various aspects herein. In some embodiments, the passive sensor circuit 1502 can include a graphene varactor (variable capacitor) or metal-graphene-oxide capacitor 1504 (wherein RS represents the series resistance and CG represents the varactor capacitor) coupled to an inductor 1510. Graphene varactors can be prepared in various ways and with various geometries. As just one example, in some aspects, a gate electrode can be recessed into an insulator layer. A gate electrode can be formed by etching a depression into the insulator layer and then depositing an electrically conductive material in the depression to form the gate electrode. A dielectric layer can be formed on a surface of the insulator layer and the gate electrode. In some examples, the dielectric layer can be formed of a material, such as, aluminum oxide, hafnium dioxide, zirconium dioxide, hafnium silicate or zirconium silicate. A graphene layer can be disposed on the dielectric layer. In some aspects, the graphene layer can be a graphene monolayer. Contact electrodes can also be disposed on a surface of the graphene layer. Aspects of exemplary graphene varactors 1504 can be found in U.S. Publ. App. No. 2014/0145735, the content of which is herein incorporated by reference.

In various embodiments, the functionalized graphene layer (e.g., functionalized to include analyte binding receptors), which is part of the graphene varactor and thus part of a sensor circuit such as a passive sensor circuit, is exposed to the gas sample flowing over the surface of the measurement zone. The passive sensor circuit 1502 can also include an inductor 1510. In some embodiments, only a single varactor is include with each passive sensor circuit 1502. In other embodiments, multiple varactors are included, such as in parallel, with each passive sensor circuit 1502.

In the passive sensor circuit 1502, the quantum capacitance of the electrical circuit changes upon binding between the analyte binding receptors and a component from a gas sample. The passive sensor circuit 1502 can function as an LRC resonator circuit, wherein the resonant frequency of the LRC resonator circuit changes upon binding with a component from a gas sample.

The reading circuit 1522 can be used to detect the electrical properties of the sensor circuit 1502. By way of example, the reading circuit 1522 can be used to detect the resonant frequency of the LRC resonator circuit and/or changes in the same. In some embodiments, the reading circuit 1522 can include a reading coil having a resistance 1524 and an inductance 1526. When the sensor-side LRC circuit is at its resonant frequency, a plot of the phase of the impedance of the reading circuit versus the frequency has a minimum (or phase dip frequency). Sensing can occur when the varactor capacitance varies in response to binding of analytes, which changes the resonant frequency, and the value of the phase dip frequency.

Figure 16:
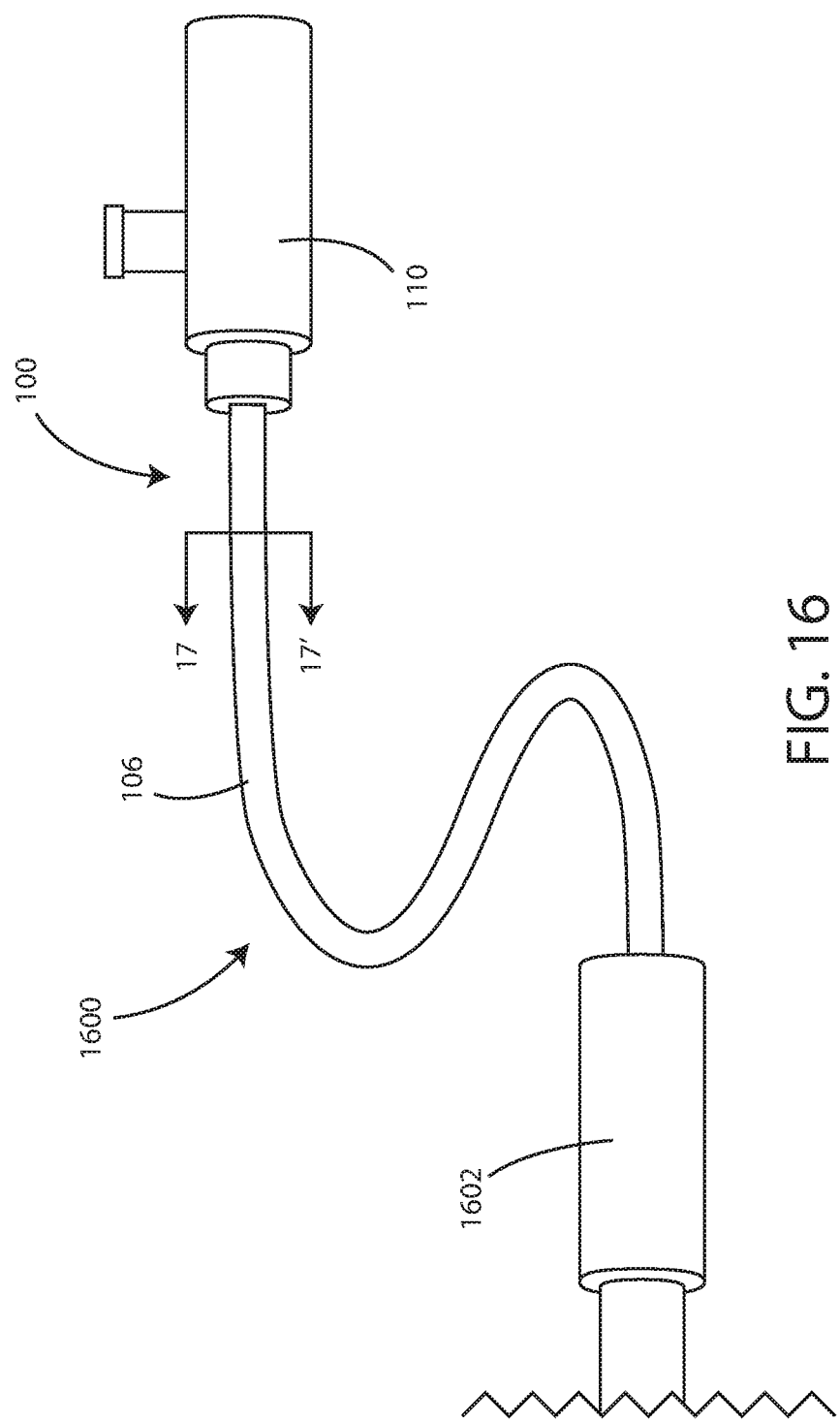
FIG. 16 is a schematic view of an apparatus for sampling gases in a patient in accordance with various embodiments herein.

Referring now to FIG. 16, a schematic view is shown of an apparatus 1600 for sampling gases in a patient in accordance with various embodiments herein. The apparatus 1600 can include a gas sampling catheter 100, including a catheter shaft 106. The apparatus 1600 can also include a device 1602 (such as an endoscope or a bronchoscope). The device 1602 can include a lumen and the gas sampling catheter 100 can be disposed within the lumen of the device 1602.

Figure 17:
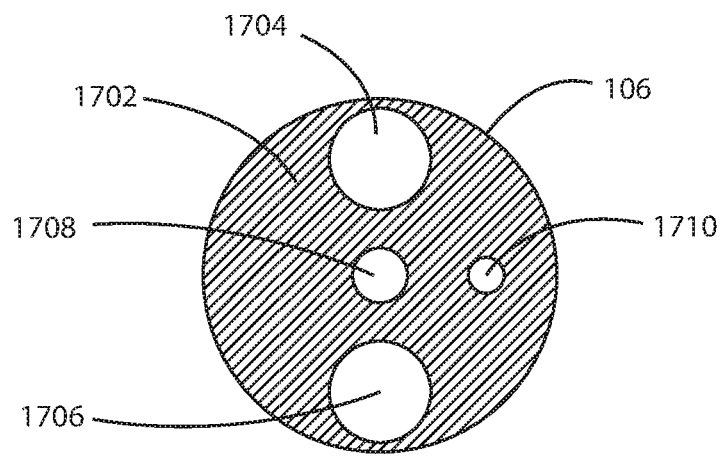
FIG. 17 is a cross-sectional view of a gas sampling catheter shaft in accordance with various embodiments herein.

Gas sampling catheter shafts can have various configurations in cross-section. Referring now to FIG. 17, a cross-sectional view of a gas sampling catheter shaft 106 is shown in accordance with various embodiments herein. The catheter shaft 106 can include a solid portion 1702 and can define a first gas flow path 1704 (or channel or lumen). The solid portion 1702 can be formed of various materials. In some embodiments, the solid portion 1702 is a polymer such as a polyamide, PEBAX, polyurethane, polyolefin, polyvinylchloride, or the like. In some embodiments, the catheter shaft 106 can also define a second gas flow path 1706 (or channel or lumen). In some embodiments, the catheter shaft 106 can define an additional lumen 1708 that can be used for various purposes including the passage of a guide wire there through. In some embodiments, the catheter shaft 106 can define a lumen 1710 that can be used for the passage of electrical conductors, such as wires or traces, there through.

The diameter of the gas sampling catheter shaft 106 can vary. In some embodiments, the diameter can be about 0.5 mm to about 5 mm.

Figure 18:
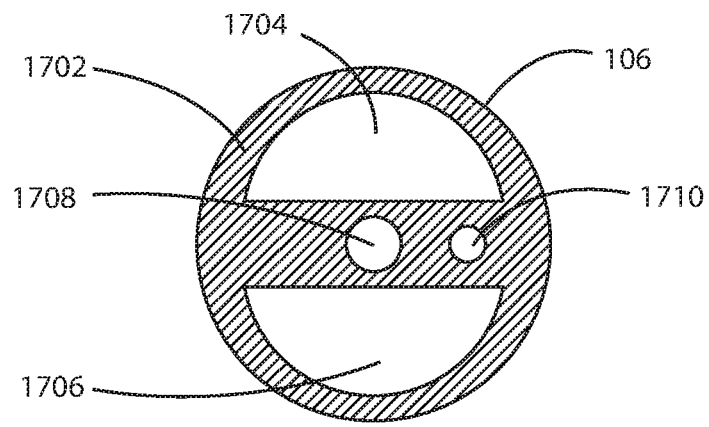
FIG. 18 is a cross-sectional view of a gas sampling catheter shaft in accordance with various embodiments herein.

It will be appreciated that the lumens, such as the gas flow paths, can have various shapes in cross-section. By way of example, the lumens can be circular, oval, polygonal, irregular, or the like. Referring now to FIG. 18, a cross-sectional view of a gas sampling catheter shaft 106 is shown in accordance with various embodiments herein. In this embodiment, the catheter shaft 106 defines a first gas flow path 1704, a second gas flow path 1706, and lumens 1708 and 1710. In this embodiment, the first gas flow path 1704 and the second gas flow path 1706 are each semi-circular and have a substantially flat inner surface.

Figure 19:
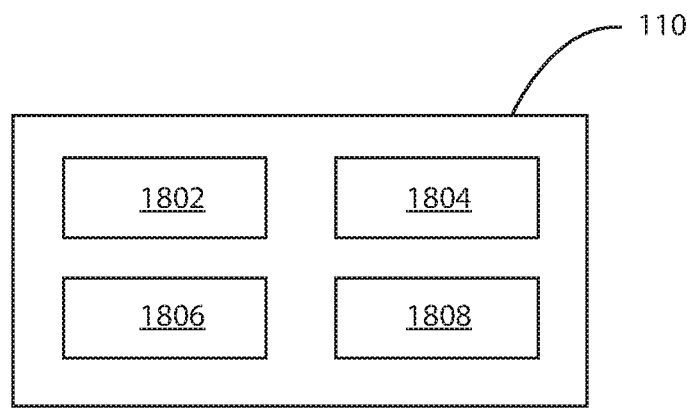
FIG. 19 is a schematic diagram of various components of a proximal housing in accordance with various embodiments herein.

In various embodiments, the gas sampling catheter can include a housing (or proximal housing) disposed on the proximal end. The housing can include various components related to the functioning of the gas sampling catheter. In some embodiments, the proximal housing can be detachable from the catheter shaft. In some embodiments, the proximal housing can be reusable and the catheter shaft can be disposable. In some embodiments, the entire gas sampling catheter can be disposable. Referring now to FIG. 19, a schematic diagram of various components of a proximal housing 110 is shown in accordance with various embodiments herein. The proximal housing 110 can include, in some embodiments, one or more of a source of negative air pressure (or vacuum generator) 1802, a processor 1804, a sensor interface circuit 1806, and a power supply circuit 1808. It will be appreciated, however, that some embodiment may include different components, additional components, or fewer components.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

Aspects have been described with reference to various specific and preferred embodiments and techniques. However, it should be understood that many variations and modifications may be made while remaining within the spirit and scope herein.

The invention claimed is:

1. A gas sampling catheter comprising
a catheter shaft having a proximal end and a distal end, the catheter shaft defining a gas flow channel therein,
an aperture defining a gas sampling port disposed at the distal-most end of the catheter shaft to provide direct fluid communication between an exterior of the catheter shaft adjacent the distal-most end of the gas flow channel of the catheter shaft; and
a plurality of individual sensor elements disposed in series with one another within the gas flow channel and wherein each individual sensor element is separated by gaps between the individual sensor elements, each one of the plurality of individual sensor elements configured to detect one or more analytes of a gaseous sample drawn from an inside of a patient;
wherein each one of the plurality of individual sensor elements comprise one or more measurement zones, each measurement zone within the individual sensor elements comprising a plurality of discrete binding detectors disposed in a dimensional array within each measurement zone, each discrete binding detector ordered across a length and width of each measurement zone, and each discrete binding detector comprising analyte binding receptors configured for binding the one or more analytes of the gaseous sample;
wherein the aperture defining a gas sampling port is configured to convey a gas phase sample from inside the patient and through the gas flow channel to the plurality of sensor elements as a flow of gas; and
wherein the gas sampling catheter does not include a porous membrane disposed over the gas flow channel.

2. The gas sampling catheter of claim 1, further comprising a filter element disposed in the gas flow channel between the gas sampling port and the sensor element.

3. The gas sampling catheter of claim 2, the filter element comprising electrospun filter media.

4. The gas sampling catheter of claim 1, comprising a manifold structure in fluid communication with the gas sampling port, the manifold structure defining a plurality of gas flow paths.

5. The gas sampling catheter of claim 4, comprising a plurality of filter elements in fluid communication with the plurality of gas flow paths of the manifold.

6. The gas sampling catheter of claim 4, comprising a plurality of sensor elements in fluid communication with the plurality of gas flow paths of the manifold.

7. The gas sampling catheter of claim 1, comprising a plurality of sensor elements disposed serially within the gas flow channel of the catheter shaft.

8. The gas sampling catheter of claim 7, comprising a plurality of filter elements disposed serially within the gas flow channel of the catheter shaft.

9. The gas sampling catheter of claim 1, further comprising a vacuum generator in fluid communication with the proximal end of the catheter shaft.

10. The gas sampling catheter of claim 1, one or more electronic alignment elements disposed along the catheter shaft.

11. The gas sampling catheter of claim 10, wherein the one or more electronic alignment elements are indicative of the position of one or more sensor elements.

12. The gas sampling catheter of claim 1, wherein the gas sampling catheter is disposable.

13. The gas sampling catheter of claim 1, the one or more measurement zones comprising a first measurement zone defining a portion of a first gas flow path, and a second measurement zone, separate from the first measurement zone, the second measurement zone comprising a plurality of discrete binding detectors, the second measurement zone disposed outside of the first gas flow path.

14. The gas sampling catheter of claim 1, the discrete binding detectors each comprising an LRC resonator circuit.

15. The gas sampling catheter of claim 1, wherein the sensor element is disposed within a proximal housing that is in fluid communication with the gas flow channel of the gas sampling catheter.

16. The gas sampling catheter of claim 1, wherein the sensor element is disposed within the gas flow channel at a position that is inside of the patient when a gas sample is drawn.

17. The gas sampling catheter of claim 1, wherein each measurement zone can be ordered so that specific discrete binding detectors for analytes having a lower molecular weight are located a farther distance from the incoming gas phase sample relative to specific discrete binding detectors for analytes having a higher molecular weight which are located closer to the incoming gas phase sample.

18. The gas sampling catheter of claim 1, wherein each measurement zone can be ordered so that specific discrete binding detectors for analytes having a lower polarity are located a farther distance from the incoming gas phase sample and specific discrete binding detectors for analytes having a higher polarity are located closer to the incoming gas phase sample.

19. An apparatus for sampling gases in a patient comprising:
   a device selected from the group consisting of an endoscope and a bronchoscope, the device comprising a device lumen; and
   a gas sampling catheter disposed within the device lumen, the gas sampling catheter comprising
      a catheter shaft having a proximal end and a distal end, the catheter shaft defining a gas flow channel therein,
      an aperture defining a gas sampling port disposed at the distal-most end of the catheter to provide fluid communication between an exterior of the catheter shaft adjacent the distal-most end of the gas flow channel; and
      a plurality of individual sensor elements disposed in series with one another within the gas flow channel and wherein each individual sensor element is separated by gaps between the individual sensor elements, each one of the plurality of individual sensor elements configured to detect one or more analytes of a gaseous sample drawn from an inside of a patient;
   wherein each one of the plurality of individual sensor elements comprise one or more measurement zones, each measurement zone within the individual sensor elements comprising a plurality of discrete binding detectors disposed in a dimensional array within each measurement zone, each discrete binding detector ordered across a length and width of each measurement zone, and each discrete binding detector comprising analyte binding receptors configured for binding the one or more analytes of the gaseous sample;
   wherein the gas sampling catheter is configured to convey the gaseous sample directly through the gas sampling port from the inside of the patient in a gas phase; and
   wherein the gas sampling catheter does not include a porous membrane disposed over the gas flow channel.

* * * * *